United States Patent [19]

Boros et al.

[11] 4,284,727

[45] Aug. 18, 1981

[54] PROCESS FOR TREATING ANION EXCHANGE RESINS

[75] Inventors: Eugene J. Boros, South Charleston; David W. Peck, Charleston, both of W. Va.

[73] Assignee: Union Carbide Corporation, New York, N.Y.

[21] Appl. No.: 80,079

[22] Filed: Sep. 28, 1979

[51] Int. Cl.$^3$ ............................................... L08D 5/20
[52] U.S. Cl. ........................................ 521/28; 521/32
[58] Field of Search ............................. 521/28, 32, 26

[56] References Cited

U.S. PATENT DOCUMENTS 4,159,930   6/1980   Degenkolb et al. ................. 204/111

Primary Examiner—Joseph L. Schofer
Assistant Examiner—Peter F. Kulkosky
Attorney, Agent, or Firm—William Raymond Moran

[57] ABSTRACT

Process for treating anion exchange resins containing a major portion of weak-base groups in catalytically inactive salt form and a minor portion of strong-base groups in catalytically inactive salt form wherein the resin is contacted with an aqueous solution containing ammonium hydroxide and ammonium chloride.

5 Claims, No Drawings

PROCESS FOR TREATING ANION EXCHANGE RESINS

This invention relates to anion exchange resins and more particularly to a process for treating anion exchange resins used as catalysts in the production of carbamates to minimize production of undesirable by-products.

It is, of course, well known that anion exchange resins may be employed as catalysts for a wide variety of reactions. Merely as illustrative, anion exchange resins are employed as catalysts in the reactions between compounds containing isocyanate groups and hydroxide substituted organic compounds to form carbamates. In general, both weak-base and strong base anion exchange resins can be utilized as catalysts to form carbamates. As is known, weak-base resins contain amine functional groups, while strong-base resins contain quaternary ammonium functional groups. These two groups behave differently in reactions with chemicals, and often behave differently as catalysts. For example, a weak-base tertiary amine resin reacts with hydrochloric acid, changing the group to a quaternary ammonium chloride, which is normally inactive catalytically. The free base is conventionally regenerated by reaction with an inorganic base such as sodium hydroxide.

A strong-base quaternary ammonium resin in the hydroxide form also reacts with hydrochloric acid to form a quaternary ammonium chloride salt, and can conventionally be regenerated to the hydroxide form with sodium hydroxide solution. The two resins differ, however, in their reactions with inorganic salts. For example, the hydroxide function of strong-base resins can be replaced with the anions of salts such as sodium chloride, whereas sodium chloride will not react with the tertiary amine groups of weak-base resins. This fact is used analytically, when a resin contains both weak-base and strong-base functional groups, to determine the amounts of each group present. For example, the ability of the resin to take up chloride ion from sodium chloride solution is measured, to determine strong-base capacity whereas the ability to accept additional chloride from hydrochloric acid is measured to determine weak-base capacity.

For certain reactions it is desired that the anion exchange resins contain solely weak-base groups with substantially little or no strong-base groups. Unfortunately, however, it has been found that resins sold as weak-base resins do in fact have some proportion of strong-base functional groups, although this fact is often disguised because those groups are in the salt form, while the weak-base groups are in the free base form. Thus the resin initially behaves solely as a weak base resin. When it is necessary to regenerate the resin, however, this is conventionally done with sodium hydroxide solution, so the strong-base groups are converted to the hydroxide form.

The consequences of the presence of strong-base functional groups in weak-base resins is that strong-base groups catalyze undesired reactions. For example in the synthesis of 1-naphthyl methylcarbamate from 1-naphthol and methyl isocyanate, which is catalyzed by weak-base resins, such as Amberlyst A-21, Amberlite IRA-35, Duolite A-561 and Dowex MWA-1, after catalyst regeneration by conventional procedures, it was observed that large proportions of 1-naphthyl 2,4-dimethylallophanate is formed in the reaction.

Thus under conventional regeneration techniques, since the presence of strong base groups in weak base resin catalysts tend to increase the production of undesirable by-products such as allophanates, it would therefore be desirable to provide a process for treating anion exchange resins containing a major portion of weak-acid groups in catalytically inactive salt form and a minor portion of strong-base groups in catalytically inactive salt form whereby the weak-base groups are converted to their catalytically active free amine form while maintaining the strong-base groups in their catalytically inactive salt form.

Accordingly the principal object of the present invention is to provide a process for treating anion exchange resins containing a major portion of weak-base groups in catalytically inactive salt and minor portion of strong-base groups in catalytically inactive salt form whereby the weak-base groups are converted to their catalytically active free amine form while maintaining the strong-base groups in their catalytically inactive salt form.

Other objects of the present invention will become apparent from the following description of the invention.

Broadly contemplated the present invention provides a process for treating anion exchange resins containing a major portion of weak-base groups in catalytically inactive salt form and a minor portion of strong-base groups in catalytically inactive salt form which comprises contacting said anion exchange resin with an aqueous solution containing ammonium hydroxide and ammonium chloride for a time sufficient to convert said weak-base groups to their catalytically active free amine form while maintaining said strong-base groups in their catalytically inactive salt form.

In general, the anion exchange resin is treated by a technique whereby an aqueous solution containing ammonium hydroxide and ammonium chloride is directed in contact with the anion exchange resin catalyst, which is preferably contained in a column under conditions whereby the weak-base groups in salt form are converted to the free-base form and the strong-base groups remain in their catalytically inactive salt-base form.

The anion exchange resins which can be treated according to the invention can be described generically as synthetic aryl resins consisting essentially of a hydrocarbon skeleton and carrying a major portion of "weak-base" groups such as amine groups and a minor portion of "strong-base" groups such as quaternary ammonium functional groups in their salt form. The term major portion is intended to connote amounts in excess of 50% by weight whereas the term minor portion is intended to connote amounts below 50% by weight.

The mechanical structure of the resin skeleton is not critical to the practice of the invention. Illustrative of the types of backbone structures present in the applicable resins are solid cross-linked polymers of vinyl aromatic compounds, such as styrene, or vinyl toluene or cross-linked copolymers of vinyl aromatic compounds with other monoethylenically unsaturated compounds such as isobutylene, acrylonitrile or its homologues, acrylamide or its homologues and methyl acrylate or methacrylate or its higher alkyl homologues. Ion exchange resins of this type and their preparations are well known and are readily available as commercial products. For example, anion exchange resins sold by the Rohm and Haas Company under the "AMBERLITE" trademark, particularly, "Amberlite IRA-45";

"Amberlite IRA-68" and "Amberlite IRA-93", as well as "AMBERLYST A-21" sold by the same company are illustrative of useful anion exchange resins having tertiary polyamine functionality which may be used in the practice of this invention. "DOWEX MWA-1" sold by the Dow Chemical Company and "DUOLITE A-561" sold by the Diamond Alkali Chemical Company, are additional examples of this class of anion exchange resins.

The anion exchange resins useful in accordance with this invention may be either of the gel type or of the macroporous or macroreticular type.

In general, the process of this invention can be carried out by placing the anion exchange resin to be treated in a vessel and introducing into the vessel an aqueous solution containing ammonium hydroxide and ammonium chloride under conditions whereby any weak-base groups present in inactive salt form are converted to the free base form and any strong base groups which are in their catalytically inactive salt-base form are unconverted, i.e., they remain in the catalytically inactive salt form.

Since the problem becomes more pronounced at the time during which the resin serves as a catalyst, it is preferred to treat the catalyst, e.g. regenerate the catalyst in a continous flow system. Thus, particles of the ion exchange resin catalyst usually in the form of beads are contained in a column and a solution of the reactants caused to flow through the resin bed. The reaction occurs while solution is in contact with the catalyst. After the solution has passed through the catalyst bed, the product is separated from the solvent and unreacted starting materials removed by conventional means such as crystallization or distillation, as dictated by properties of the solution and its components. Solvents may be used if desired, provided they are inert to the reactants and the ion exchange resin, under the reaction conditions. The solvent selected should, adequately, dissolve both the reactants and the product at or below the reaction temperature. The solvent should not, however, be capable of dissolving the ion exchange resin catalyst. Examples of typically useful solvents are benzene, toluene, xylenes, ethyl benzene, pentane, hexane, heptanes, chloroform, and carbon tetrachloride.

Reaction temperatures for these conventional reactions are well known. As is well known, reaction temperatures are dictated largely by practical considerations depending upon the reactants employed. Typical reaction temperatures in the applicable reactions range between 20° and 100° C. Parameters which must be taken into consideration in selecting the reaction temperatures include the solubilities of reactants and product in the solvent, the boiling point of the solvent, the reaction rate, and the maximum use temperature which is practical for the ion exchange resin catalyst to achieve maximum catalyst life in a manner consistent with the achievement of the desired reaction rate. Generally, the reactions between hydroxy substituted organic compounds and compounds containing isocyanate groups are exothermic in nature and, therefore, some means, such as a water-jacketed reactor should be provided to maintain the temperature below the selected upper limit.

Pressures for these conventional reactions are also not a significant factor in the conduct of the reaction. Atmospheric pressures are quite satisfactory except that in a continuous flow system there must be provision made to provide for sufficient pressure behind the flow of the reaction solution to force it through the resin bed. Ordinarily, a pressure drop across the resin bed of less than 2 psi per foot of bed depth is satisfactory for this purpose. The flow rate in continuous flow systems is normally in the range of 1 to 50 volumes of solution per volume of ion exchange resin per hour.

It is normally desirable to maintain an essentially 1 to 1 stoichiometric ratio between the reactants except in those instances where an excess of hydroxy substituted organic compound is used as a solvent or where an incomplete reaction is desired.

After a short period of use the weak-base groups of the catalyst, although initially in free-base form are converted to the salt form which renders the catalyst substantially inactive. The strong-base groups initially were and still are in salt form and are substantially catalytically inactive. The resin must be treated to convert the weak-base groups back to the free-base form, but the treatment must prevent conversion of the strong-base groups to the hydroxide form which would increase the formation of undesirable by-product. The regeneration of the catalyst must therefore be performed with the above objectives.

According to the present invention the technique for accomplishing the above is accomplished by directing an aqueous solution containing ammonium hydroxide and ammonium chloride through the column in contact with the catalyst contained therein.

The relationship of the ratios of the ammonium hydroxide and ammonium chloride should be such that the treatment leaves substantially all of the quaternary ammonium groups (strong-base group functionality) in the chloride form and converts the chloride form of the amine groups to the free-base form. In general, this can be accomplished with a solution containing about 2 to about 12 percent by weight, preferably about 6 to about 10 percent ammonium chloride and about 1 to about 10 percent by weight, preferably about 3 to about 5 percent ammonium hydroxide.

Amounts of hydroxide substantially in excess of about 10 percent by weight result in a substantial conversion of the quaternary ammonium groups to the hydroxide form notwithstanding the presence of the ammonium chloride.

Normally the ammonium chloride concentration should be higher than the ammonium hydroxide concentration, so that, in the competition for chloride between ammonium ions in solution and quaternary ammonium ions attached to the resin, there will be sufficient chloride to insure that essentially all of the resin's quaternary ammonium groups are in the chloride form.

In an alternate but less preferred procedure, the spent catalyst is regenerated by treatment with a sodium hydroxide solution and thereafter treated with ammonium chloride solution so that any hydroxylated strong-base groups of the resin are converted back to the chloride form (catalytically inactive). By this treatment the weak-base groups of the resin remain in free form.

In general the reaction conditions, e.g. the ratios of the sodium hydroxide and ammonium chloride temperatures and pressures are the same as employed in the preferred procedure.

The temperatures and pressures utilized for the treatment of the catalyst are not critical. Ambient temperature is satisfactory, and the only limitations on temperature are that the solution components be in the liquid phase, and that the manufacturer's recommended upper temperature limit for the resin not be exceeded. The pressure need be only enough to overcome the pressure drop through the resin bed.

The following examples will illustrate the present invention. Examples II–XII demonstrate the continuous preparation of 1-naphthyl methylcarbamate and the regeneration of the "Amberlyst" A-21 catalyst. In Example I the resin was not subjected to regeneration treatment and the results shown are for the initial use of the catalyst as received from the manufacturer.

Portions (120 ml) of "Amberlyst" A-21 resin catalyst were treated by passing solutions over them as indicated in Examples II–XII. They were then thoroughly rinsed with water and dried in a vacuum oven at 60° C., after which 80 ml was slurried in toluene and transferred to the reaction column. Toluene solutions containing 8.6 percent methyl isocyanate and 17.7 percent 1-naphthol (a mole ratio of 1.23:1) were passed down the column at the rate of 600 ml per hour. The column was maintained at 80° C. by oil in the jacket. The product was collected and cooled, and after most of the carbaryl had precipitated, the remaining solution was analyzed for percent 1-naphthyl 2,4-dimethylallophanate by liquid chromatography. The results are indicated in Table I.

isocyanate and 18.0 percent 1-naphthol, (mole ratio of 1.1:1). The results are shown in the Table.

TABLE II

Regeneration of "Amberlite" XE-275 Ion Exchange Resin to Prevent Formation of 1-Naphthyl 2,4-Dimethylallophanate During Synthesis of 1-Naphthyl Methylcarbamate

| Example | Treatment Solution | Amount | 1-Naphthyl 2,4-Dimethyl-allophanate in Product Solution, % |
|---|---|---|---|
| XVII | 4% NaOH | 300 cc | 2.67 |
| XVIII | 10% NH4Cl 4% NH4OH | 200 cc | 0.04 |

Since various changes and modifications may be made in the invention without departing from the spirit thereof, the invention is deemed to be limited only by the scope of the appended claims.

What is claimed is:

1. A process for treating anion exchange resins containing a major portion of weak-base groups in catalytically inactive salt form and a minor portion of strong-base groups in catalytically inactive salt form which comprises contacting said ion exchange resin with an

TABLE I

REGENERATION TREATMENT OF AMBERLYST A-21 ION EXCHANGE RESIN TO PREVENT FORMATION OF 1-NAPHTHYL 2,4 DIMETHYLALLOPHANATE DURING SYNTHESIS OF 1-NAPHTHYL METHYLCARBAMATE.

| EXAMPLE | FIRST TREATMENT SOLUTION | AMOUNT | SECOND TREATMENT SOLUTION | AMOUNT, g | % 1-NAPHTHYL 2,4-DIMETHYL-ALLOPHANATE IN PRODUCT SOLUTION, 120-MINUTE SAMPLE |
|---|---|---|---|---|---|
| I | none | | none | | 0.1 |
| II | 4% NaOH | 300 | none | | 8.2 |
| III | 8% NaHCO3 | 300 | none | | 9.5 |
| IV | 5% Na2CO | 300 | none | | 8.5 |
| V | 10% CH3COONa | 300 | none | | 8.8 |
| VI | 8% NH4OH | 300 | none | | 4.3 |
| VII | 4% NaOH | 300 | 1% NaCl | 100 | 5.1 |
| VIII (1) | 4% NaOH | 300 | 10% NaCl | 500 | 0.9 |
| IX (1) | 4% NaOH | 300 | 10% CaCl2 | 500 | 0.8 |
| X | 4% NaOH | 300 | 5% NH4Cl | 100 | 0.1 |
| XI (2) | 9% NH4OH / 10% NH4Cl | 200 | none | | 0.2 |
| XII (2) | 4% NH4OH / 10% NH4Cl | 400 | none | | 0.1 |

(1) 80 instead of 120 ml of resin was treated in this case.
(2) 100 instead of 120 ml of resin was treated in this case.

Examples XVII and XVIII which follow illustrate the regeneration treatment of "Amberlite" XE-275. The ion exchange resin prior to treatment contained a major portion of weak-base functional groups in catalytically inactive salt form and a minor portion of strong-base groups in the form of quaternary ammonium functional groups in catalytically inactive salt form.

The procedure utilized was substantially identical to the procedure for the treatment and regeneration of "Amberlyst" A-21 and the method of producing 1-naphthyl methylcarbamate according to Examples II–XII, except that the amount of resin was 100 cc, and water was removed by solvent exchange. The ion exchange resin utilized was "Amberlite" XE-275 available from the Rohm & Haas Co. The resin was regenerated with 4% sodium solution for Example XVII and a 10% ammonium chloride/4% ammonium hydroxide solution for Example XVIII.

Before the reaction step, 200 cc of a 7.5 percent solution of methyl isocyanate was passed through the resin bed. The reaction solution contained 7.8 percent methyl isocyanate and 18.0 percent 1-naphthol, (mole ratio of 1.1:1). The results are shown in the Table.

aqueous solution containing ammonium hydroxide and ammonium chloride for a time sufficient to convert said weak-base groups to their catalytically active free amine form while maintaining said strong-base groups in their catalytically inactive salt form, wherein said aqueous solution contains from about 2 to about 12 percent by weight ammonium chloride and from about 1 to about 10 percent ammonium hydroxide.

2. A process according to claim 1 wherein said catalytically inactive salt form of said weak-base groups is the chloride salt form.

3. A process according to claim 1 wherein said anion exchange resin has a resin skeleton consisting essentially of a solid cross-linked polymer of a vinyl aromatic composition.

4. A process according to claim 1 wherein said aqueous solution contains an ammonium chloride concentration by weight in excess of said ammonium hydroxide.

5. A process according to claim 4 wherein said aqueous solution contains from about 6 to about 10 percent by weight ammonium chloride and from about 3 to about 5 percent by weight ammonium hydroxide.

* * * * *